United States Patent [19]

Lattek et al.

[11] Patent Number: 4,621,521
[45] Date of Patent: Nov. 11, 1986

[54] APPARATUS FOR DETERMINING FOAM FORMATION OF CRUDE PETROLEUM

[75] Inventors: Horst Lattek; Hans-Ferdi Fink; Götz Koerner, all of Essen, Fed. Rep. of Germany

[73] Assignee: Th. Goldschmidt AG, Essen, Fed. Rep. of Germany

[21] Appl. No.: 704,372

[22] Filed: Feb. 22, 1985

[30] Foreign Application Priority Data

Feb. 25, 1984 [DE] Fed. Rep. of Germany ... 8405787[U]

[51] Int. Cl.$^4$ ............................................. G01N 33/28
[52] U.S. Cl. ..................................................... 73/60.1
[58] Field of Search .......................................... 73/60.1

[56] References Cited

U.S. PATENT DOCUMENTS 3,027,755 4/1962 Groll, Jr. et al. ..................... 73/60.1
3,107,519 10/1963 McGinn ................................. 73/60.1

FOREIGN PATENT DOCUMENTS 735795 5/1943 Fed. Rep. of Germany ....... 73/60.1
2551260 5/1977 Fed. Rep. of Germany ....... 73/60.1

Primary Examiner—Stewart J. Levy
Assistant Examiner—Joseph W. Roskos
Attorney, Agent, or Firm—Toren, McGeady, Stanger, Goldberg & Kiel

[57] ABSTRACT

An apparatus for simulating the actual conditions of foam formation during crude oil production includes a transparent cylindrical measuring vessel having a circumferential flange formed at its open top. A ring-shaped member is seated on the flange and defines a chamber in communication with the measuring vessel. The ring-shaped member and the measuring vessel are connected in a gas-tight manner. A supply line for the liquid to be dissolved or distributed in the crude oil sample and a discharge line for the liquid evaporating under measurement conditions open into the chamber. The supply line is connected to a supply reservoir via a metering valve for the liquid. A stop valve is provided in the discharge line.

14 Claims, 3 Drawing Figures

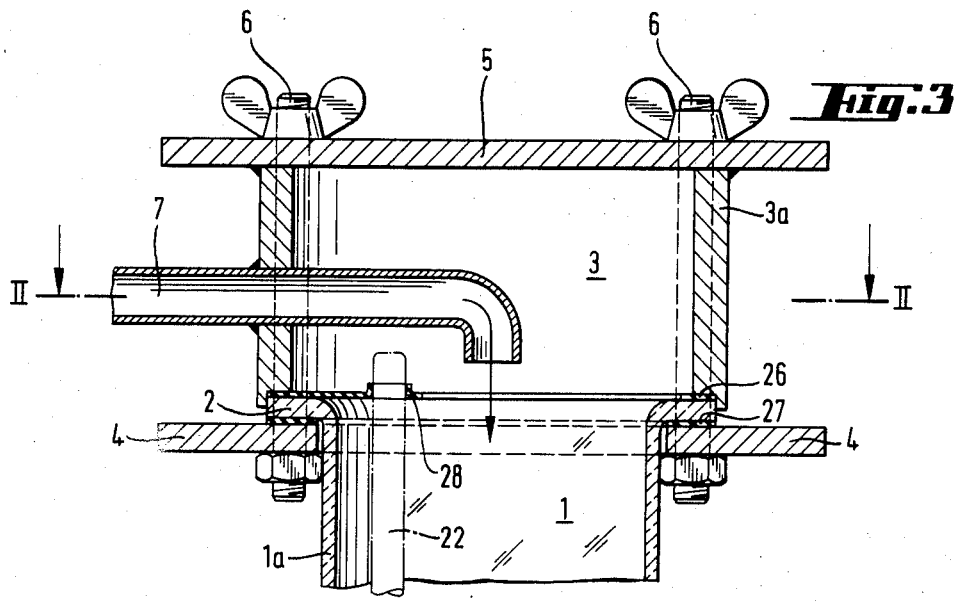
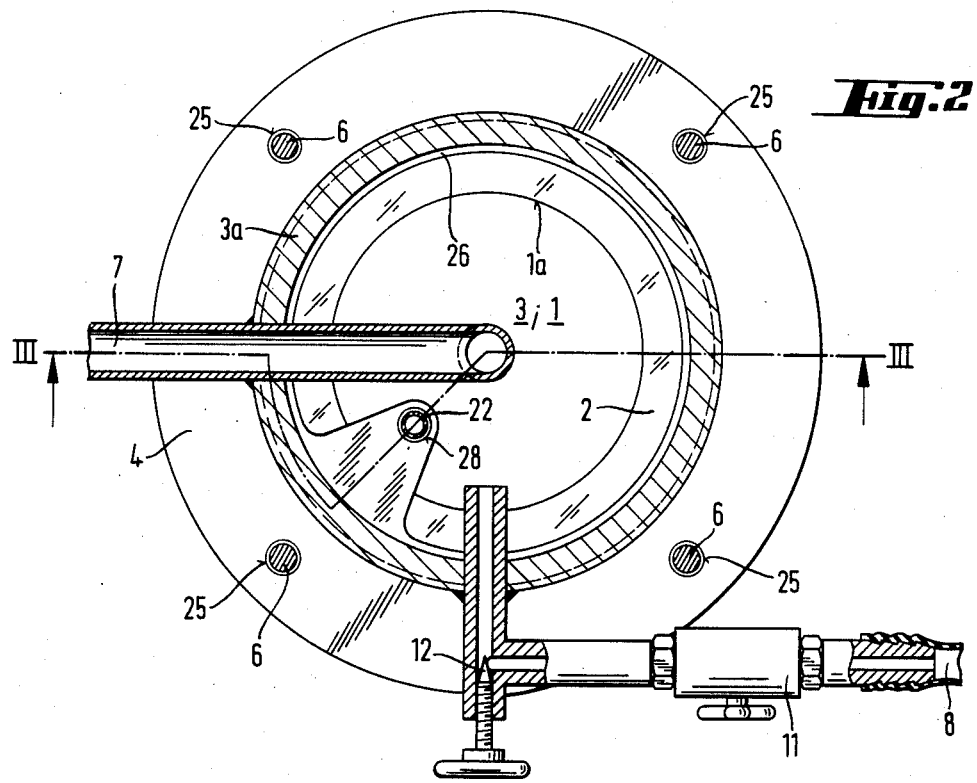

001
APPARATUS FOR DETERMINING FOAM FORMATION OF CRUDE PETROLEUM

BACKGROUND OF THE INVENTION

The present invention relates to an apparatus for determining the foam formation of crude petroleum during blowing or distilling off of liquids which are dissolved or finely distributed in the crude petroleum and which boil under testing conditions.

As a rule, crude petroleum is under considerable pressure when stored in deposits. This high pressure causes hydrocarbons to be dissolved in the crude petroleum. Since the pressure of the crude petroleum is reduced during its production, the dissolved hydrocarbons escape from the crude petroleum. During blowing off of the low-boiling hydrocarbons, the crude petroleum foams more or less intensely. The stability and quantity of the foam depend on the place of origin of the crude petroleum, its viscosity and particularly the quantity of low-boiling hydrocarbons contained in the crude petroleum. This foam formation frequently creates considerable problems during production and storage of crude petroleum.

In order to prevent or reduce the formation of foam and to decrease the stability of the foam, it is known to add chemicals to the crude petroleum as it is produced.

Even though the practical usefulness of an anti-foaming agent can be actually determined only during its use at the production site, it is desirable to make a preliminary selection under laboratory conditions of compounds which are expected to be suitable. For this purpose, it necessary to simulate the conditions of foam generation and elimination as close to the actual conditions as possible.

A method for determining the effectiveness of anti-foaming agents for crude petroleum is known. In accordance with this method, foam is generated by conducting air or natural gas through a sample of crude petroleum. After shutting off the gas supply, the foam level is measured in certain time intervals and plotted in a diagram over time. The area below the curve represents a measure for the lifetime of the foam. When tests are performed, the lifetime of the foam of an untreated sample of crude petroleum is compared to the lifetimes of foams in samples containing various anti-foaming agents and samples containing different quantities of anti-foaming agents. A decreasing lifetime of the foam indicates an increased efficiency of the anti-foaming agent.

In the above-described method, the criterion of the measurement is the period of time it takes for the already formed foam to disintegrate. However, during actual production, new foam is continuously formed during blowing off of liquids, so that it is important to evaluate the foam formation and to find ways to prevent the generation of foam.

It is, therefore, an object of the invention to provide an apparatus for accurately simulating the actual conditions under which foam is generated and prevented or eliminated.

SUMMARY OF THE INVENTION

In accordance with the present invention, the apparatus for simulating the actual conditions of foam formation during crude oil production includes a transparent cylindrical measuring vessel with a closed bottom and an open top, wherein a circumferential flange is formed at the open top. A ring-shaped member seated on the flange defines a chamber in communication with the measuring vessel. The top end of the chamber is formed by a sealing plate and the chamber is rendered gas-tight by means of a clamping ring engaging under the flange and by clamping screws extending in axial direction of the measuring vessel. Sealing rings are provided on the top and bottom surfaces of the flange. A supply line for the liquid to be dissolved or distributed in the crude oil sample and a discharge line for the liquid evaporating under measurement conditions open into the chamber. The supply line is connected to a supply reservoir via a metering valve for the liquid. A stop valve is provided in the discharge line.

In accordance with a preferred embodiment of the invention, a needle valve is arranged in the discharge line upstream of the stop valve. The needle valve makes it possible to limit and adjust the quantity of gas escaping per unit of time under measurement conditions. Preferably, the needle valve is arranged directly in the chamber above the measuring vessel.

A flow meter may be arranged in the discharge line in order to control the blow off velocity.

It is advantageous to arrange a pressure indicator in the supply line for the liquid in order to make it possible to detect any dependency of the behavior of the foam on the pressure.

In order to avoid that an unduly high pressure is built up in the glass apparatus, a bypass line is provided which connects the supply line and the discharge line. A safety valve in the bypass line permits gas flow through the bypass line when a given maximum pressure in the measuring vessel is exceeded.

Scale markings are provided on the transparent measuring vessel, so that the level of the generated foam can be determined.

In accordance with another feature of the invention, to enable comparative measurements under exactly comparable conditions, the temperature in the measuring vessel can be controlled. To this end, the measuring vessel is surrounded by a temperature control vessel containing a heat transfer medium.

The desired measurement temperature is advantageously adjusted and controlled by means of a heating unit. This heating unit may additionally be part of a magnetic stirrer. The magnetic stirrer moves magnetic stirring cores which agitate the heat transfer medium and the crude petroleum sample to be tested.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in where there are illustrated and described preferred embodiments of the invention.

BRIEF DESCRIPTION OF THE DRAWINGS

In the drawings:

FIG. 2 is an enlarged horizontal sectional view of the apparatus shown in FIG. 1 along sectional line II—II of FIG. 3; and FIG. 3 is an enlarged vertical sectional view of the apparatus shown in FIG. 1 along sectional line III—III of FIG. 2.

DETAILED DESCRIPTION OF THE INVENTION

Figure 1:
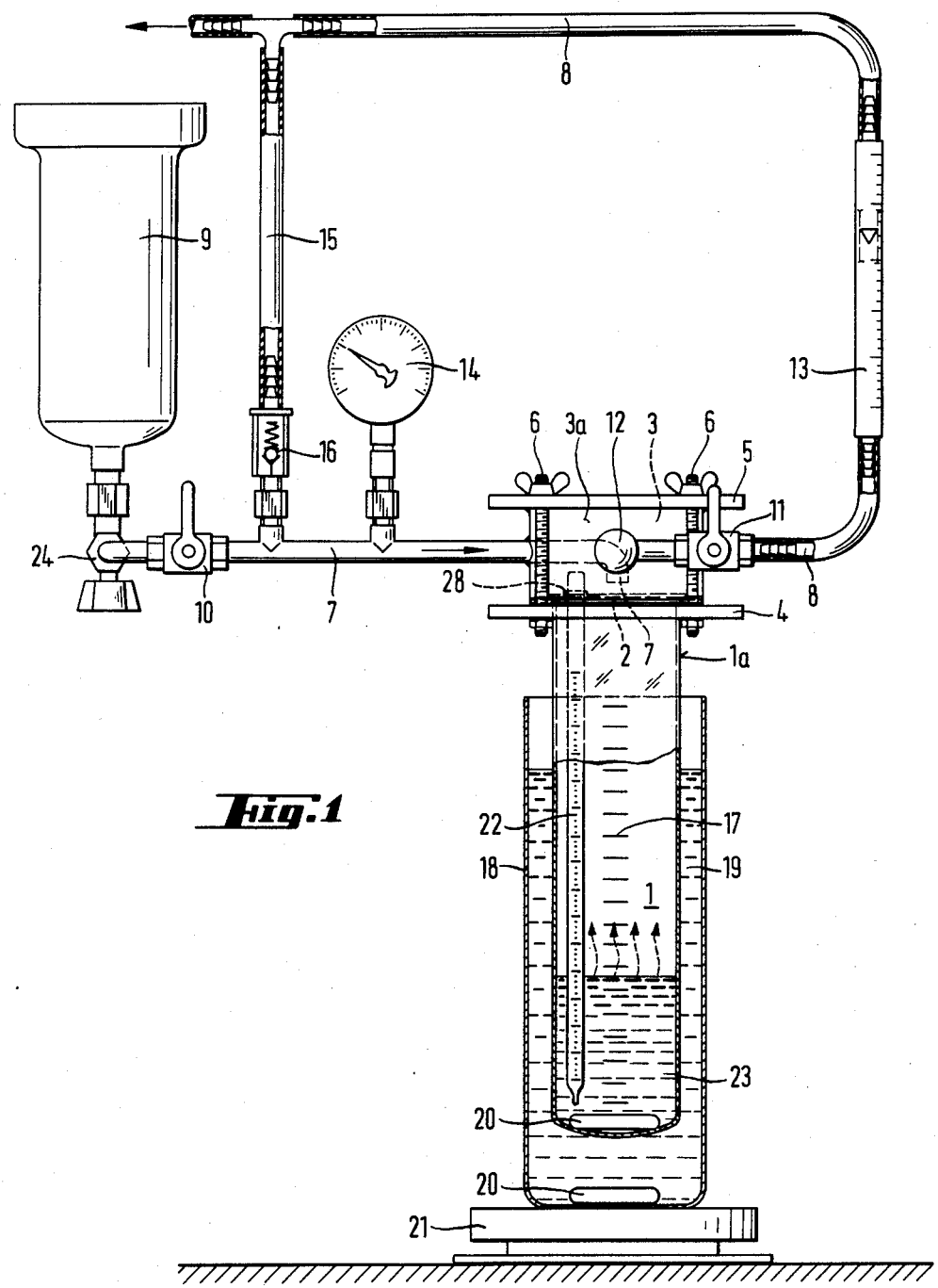
FIG. 1 is a front elevational view, partially in section, of the apparatus according to the present invention.

As illustrated in FIG. 1, the apparatus according to the invention includes a measuring vessel 1 which is formed by a glass cylinder 1a which is closed at the bottom and open at the top. The wall thickness of glass cylinder 1a is selected such that it can withstand a pressure of approximately 10 bars. Measuring cylinder 1a has in its top region a flange 2, with a clamping ring 4 engaging under flange 2. A ring-shaped member 3a which defines a chamber 3 is placed on flange 2. Clamping screws 6 bias a sealing plate 5 against clamping ring 4. A plane-surface grinding may be performed on the annular contact surfaces of ring-shaped member 3a in order to obtain a good sealing action. It is also possible, as illustrated in the drawings, to provide a welded connection between sealing plate 5 and ring-shaped member 3a. A thermometer 22 is inserted in eye 28 of sealing ring 26.

A supply line 7 leads into chamber 3. This supply line 7 is in communication with a liquid gas supply reservoir 9. Reservoir 9 can be opened and closed by means of valve 24. The liquid gas is metered by means of valve 10 in supply line 7. A pressure gauge 14 is arranged between metering valve 10 and chamber 3.

A discharge line 8 for gas which escapes during testing conditions leads out of chamber 3. A stop valve 11 is arranged in discharge line 8. This stop valve 11 is constructed as a quick-action stop valve. Discharge line 8 is in communication with chamber 3 via a needle valve 12. A flow meter 13 is arranged in discharge line 8. A bypass line 15 including safety valve 16 connects supply line 7 and discharge line 8. This safety valve opens when a maximum permissible pressure in measuring vessel 1 is exceeded.

Measuring vessel 1 is surrounded by a temperature controllable vessel 18 which is filled with a heat transfer liquid 19. Heating plate 21 may also be used as a magnetic stirring element which moves magnetic stirring cores 20. Measuring vessel 1a also contains the thermometer 22 which, as already mentioned, is fastened at eye 28.

FIG. 2 is a horizontal sectional view through chamber 3 at needle valve 12 and supply line 7. Chamber 3 is placed on top of flange 2 of glass cylinder 1a. Clamping ring 4 has bores 25 into which clamping screws 6 are inserted. Supply line 7 as well as needle valve 12 extend through the wall of chamber 3.

FIG. 3 is a vertical sectional view through chamber 3. Clamping ring 4 engages under flange 2 of measuring vessel 1. Chamber 3 is placed on top of flange 2 and has in its lower portion a circumferential shoulder which facilitates centering of ring-shaped member 3a on flange 2. Screws 6 serve to tighten the top portion of the apparatus according to the invention. Approximately in the center of chamber 3, supply line 7 is bent downwardly.

In operation, a measurement is carried out by means of the apparatus according to the invention by filling into measuring vessel 1 the desired quantities of a crude petroleum sample and the anti-foaming agent to be examined. Subsequently, clamping ring 4 is slid under flange 2 of glass cylinder 1a, chamber 3 and sealing plate 5 are placed on top of flange 2, and the entire top portion is screwed gas-tight by means of screws 6. Measuring vessel 1 is then lowered into temperature controlled vessel 18 which contains heat transfer medium 19. If necessary, heat is supplied by means of heating unit 21 and heat transfer liquid 19 and the crude petroleum sample 23 are stirred by means of the magnetic stirring cores 20 until thermometer 22 indicates the desired temperature. While keeping valve 10 closed, stop valve 24 of liquid gas supply reservoir 9 is opened. When metering valve 10 is then carefully opened, liquid gas, for example liquified propane gas, flows through supply line 7 into measuring vessel 1. Metering valve 10 is closed as soon as it can be seen at markings 17 of measuring vessel 1 that the required quantity of liquid gas has been introduced into measuring vessel 1. The sample 23 to be tested is then mixed by means of magnetic stirring core 20 contained in measuring vessel 1. Depending upon the type of liquid gas used, its quantity and temperature, a certain pressure is reached which is indicated at pressure gauge 14. Stop valve 11 is now opened while needle valve 12 remains closed. Subsequently, needle valve 12 is opened carefully. The evaporating liquid gas escapes through discharge line 8. The flow velocity in discharge line 8 can be measured by means of flow meter 13. The desired flow velocity is set by means of needle valve 12 and is maintained constant during the measurement. When the liquid gas which is distilled off is blown off, a foam is generated. This foam is generated in part in the interior of the liquid and in part as gas bubbles pass through the surface of the crude petroleum. The quantity of foam can now be determined in dependence upon the period of time by means of the markings 17.

The apparatus in accordance with the present invention makes it possible to determine the quantity of foam which has been formed in dependence upon the antifoaming agent used, the temperature, the rate of blowing off of the gas, and in dependence upon the pressure, as is known in the art.

If an impermissibly high pressure is reached under unfavorable conditions, for example, when the needle valve is clogged, safety valve 16 permits flow of the gaseous hydrocarbons when a given maximum pressure is exceeded.

The apparatus in accordance with the present invention is portable and, therefore, makes it possible to test the efficiency of foam-preventing agents at the place of application, for example, on a drilling island or at intermediate storage facilities for crude petroleum.

While specific embodiments of the invention have been shown and described in detail to illustrate the application of the inventive principles, it will be understood that the invention may be embodied otherwise without departing from such principles.

We claim:

1. An apparatus for simulating the formation of foam during crude oil production, comprising a transparent cylindrical measuring vessel receiving a crude oil sample, said measuring vessel having a closed bottom and an open top, a circumferential radially extending flange having top and bottom sides formed at said open top, a ring-shaped member seated on said top side of and in coaxial relationship to said flange, said ring-shaped member defining a chamber in communication with said measuring vessel, a sealing plate placed on said ring-shaped member forming the top end of said chamber, clamping means for clamping said sealing plate against said ring-shaped member and said ring-shaped member against said top side of said flange in a gas-tight manner, a supply line for supplying liquid gas to be dissolved or distributed in the crude oil sample and a discharge line for the liquid evaporating under measurement conditions opening into said chamber, said supply line connected to a supply reservoir for said liquid, a metering valve for said liquid provided in said supply line, and control means for controlling the discharge velocity of said evaporating liquid in said discharge line.

2. The apparatus of claim 1, wherein said clamping means comprises a clamping ring placed against said bottom side of said flange and a plurality of clamping screws extending in axial direction of said measuring vessel from said sealing plate to said clamping ring.

3. The apparatus of claim 2, comprising sealing rings placed on said top and bottom sides of said flange to effect a gas-tight sealing action between said top side of said flange and said ring-shaped member and between said clamping ring and said bottom side of said flange.

4. The apparatus of claim 1, comprising a flow meter in said discharge line.

5. The apparatus of claim 1, comprising a pressure gauge in said supply line.

6. The apparatus of claim 1, comprising a by-pass line extending between said supply line and said discharge line, said by-pass line including a safety valve permitting flow through said by-pass line when a given maximum pressure is exceeded in said measuring vessel.

7. The apparatus of claim 1, comprising markings on said measuring vessel for determining the quantity of foam formed in said vessel.

8. The apparatus of claim 1, comprising means for adjusting the temperature in said measuring vessel.

9. The apparatus of claim 8, wherein said temperature adjusting means comprises a temperature controlled vessel surrounding said measuring vessel, said temperature controlled vessel containing a heat transfer medium.

10. The apparatus of claim 9, comprising magnetic cores acting as stirrers in said measuring vessel and in said temperature controlled vessel, wherein said cores additionally serve as heating units.

11. The apparatus of claim 1 wherein a stop valve is provided in said discharge line.

12. The apparatus of claim 1 wherein said control means is a needle valve.

13. The apparatus of claim 12, wherein said needle valve is upstream of said stop valve.

14. The apparatus of claim 12, wherein said needle valve is situated within said chamber.

* * * * *